United States Patent
Ghabour

(10) Patent No.: US 10,785,303 B2
(45) Date of Patent: Sep. 22, 2020

(54) DATA CENTER SELECTION FOR COMMUNICATION WITH AN INDUSTRIAL TESTING DEVICE

(71) Applicant: OLYMPUS AMERICA INC., Center Valley, PA (US)

(72) Inventor: Ehab Ghabour, Northborough, MA (US)

(73) Assignee: OLYMPUS AMERICA INC., Center Valley, PA (US)

( * ) Notice: Subject to any disclaimer, the term of this patent is extended or adjusted under 35 U.S.C. 154(b) by 9 days.

(21) Appl. No.: 15/941,656

(22) Filed: Mar. 30, 2018

(65) Prior Publication Data

US 2018/0309828 A1 Oct. 25, 2018

Related U.S. Application Data

(60) Provisional application No. 62/488,236, filed on Apr. 21, 2017.

(51) Int. Cl.
*H04L 29/08* (2006.01)
*H04W 4/70* (2018.01)
(Continued)

(52) U.S. Cl.
CPC ...... *H04L 67/1097* (2013.01); *A61B 1/00016* (2013.01); *A61B 8/42* (2013.01);
(Continued)

(58) Field of Classification Search
CPC . H04L 67/18; H04L 45/126; H04L 29/08225; H04L 67/1021; H04W 4/02;
(Continued)

(56) References Cited

U.S. PATENT DOCUMENTS 7,428,750 B1 * 9/2008 Dunn ............... G06F 21/41
726/8
7,941,669 B2 * 5/2011 Foley ............... H04L 63/083
713/182

(Continued)

FOREIGN PATENT DOCUMENTS

| EP | 3147655 A1 | 3/2017 |
| EP | 3393105 A1 | 10/2018 |
| EP | 3393105 B1 | 2/2020 |

OTHER PUBLICATIONS

"European Application Serial No. 18166872.4, Extended European Search Report dated Jun. 22, 2018", 7 pgs.

(Continued)

*Primary Examiner* — George C Neurauter, Jr.

(74) *Attorney, Agent, or Firm* — Schwegman Lundberg & Woessner, P.A.

(57) ABSTRACT

The invention relates to an industrial testing device communicating with a data center located in a remote computer network, such as the cloud. Disclosed is a method of registering the device to the cloud and specifying the geographical location of the data center. The method includes selecting a data center from a list of available data centers based on regulations specific to a device type of the industrial testing device. Features are configured for communication between the device and the selected data center.

17 Claims, 5 Drawing Sheets

(51) Int. Cl.

| | | |
|---|---|---|
| *H04L 12/733* | (2013.01) | |
| *H04W 4/024* | (2018.01) | |
| *H04W 4/029* | (2018.01) | |
| *A61B 1/00* | (2006.01) | |
| *A61B 8/00* | (2006.01) | |
| *H04L 12/24* | (2006.01) | |
| *A61B 17/00* | (2006.01) | |

(52) U.S. Cl.
CPC ...... *A61B 8/4472* (2013.01); *H04L 29/08225* (2013.01); *H04L 41/22* (2013.01); *H04L 45/126* (2013.01); *H04L 67/10* (2013.01); *H04L 67/1021* (2013.01); *H04L 67/12* (2013.01); *H04L 67/18* (2013.01); *H04W 4/024* (2018.02); *H04W 4/029* (2018.02); *H04W 4/70* (2018.02); *A61B 2017/00221* (2013.01)

(58) Field of Classification Search
CPC ....... H04W 4/04; H04W 4/043; H04W 4/046; H04W 4/024; H04W 4/029; A61B 8/00; A61B 8/42; A61B 8/4472; A61B 2017/00221; A61B 1/00016

See application file for complete search history.

(56) References Cited

U.S. PATENT DOCUMENTS

| | | | | |
|---|---|---|---|---|
| 8,125,311 | B2* | 2/2012 | Takimoto | A61B 8/00 340/5.2 |
| 8,457,990 | B1* | 6/2013 | Reicher | G06Q 10/10 705/3 |
| 8,527,633 | B2* | 9/2013 | Bade | G06F 8/61 709/225 |
| 8,676,593 | B2* | 3/2014 | Nagpal | G06Q 30/02 705/1.1 |
| 9,300,539 | B2* | 3/2016 | DeJana | H04L 41/12 |
| 9,374,228 | B2* | 6/2016 | Pendarakis | H04L 63/062 |
| 9,569,476 | B2* | 2/2017 | Dejana | G06F 3/0631 |
| 9,943,290 | B2* | 4/2018 | Jin | A61B 8/565 |
| 10,192,032 | B2* | 1/2019 | Himsl | G16H 30/20 |
| 2002/0023059 | A1* | 2/2002 | Bari | G06F 21/41 705/76 |
| 2003/0009102 | A1* | 1/2003 | Quistgaard | A61B 5/0402 600/446 |
| 2004/0141661 | A1* | 7/2004 | Hanna | G06F 19/321 382/305 |
| 2008/0208046 | A1* | 8/2008 | Pierce | A61B 8/00 600/437 |
| 2013/0036217 | A1 | 2/2013 | Dejana et al. | |
| 2015/0338858 | A1* | 11/2015 | Bates | B60P 3/20 62/56 |
| 2015/0347701 | A1 | 12/2015 | Atkin | |
| 2016/0100824 | A1* | 4/2016 | Kim | A61B 8/13 600/437 |
| 2016/0269236 | A1* | 9/2016 | Chan | H04L 41/0816 |
| 2018/0199920 | A1* | 7/2018 | Jin | A61B 8/565 |
| 2018/0271483 | A1* | 9/2018 | Nikoozadeh | A61B 8/4427 |

OTHER PUBLICATIONS

"European Application Serial No. 18166872.4, Intention to Grant dated Oct. 4, 2019", 21 pgs.

"European Application Serial No. 18166872.4, Response filed Apr. 20, 2019 to Extended European Search Report dated Jun. 22, 2018", 20 pgs.

* cited by examiner

DATA CENTER SELECTION FOR COMMUNICATION WITH AN INDUSTRIAL TESTING DEVICE

CROSS-REFERENCE TO RELATED APPLICATIONS

This application claims the benefit and priority of U.S. Provisional patent application Ser. No. 62/488,236 filed Apr. 21, 2017 entitled DATA STORAGE LOCALIZATION SELECTION FOR NDT INSPECTION, the entire disclosure of which is incorporated herein by reference.

FIELD OF THE INVENTION

The invention relates in general to communication between non-destructive testing devices and the cloud, and in particular to a method of selecting the location of an appropriate data storage center for a device registered to a cloud user account.

BACKGROUND OF THE INVENTION

Industrial measurement devices, such as X-ray fluorescence (XRF) or ultrasound devices, are often used by enterprises which deploy multiple devices worldwide in multiple different geographic locations. A device which is communicating with the cloud may transmit or receive data from a data center anywhere in the world, and in existing practice the user has no control over the geographic location of the data center.

A first problem arising from such lack of user control is that there may be local government privacy laws or corporate rules of confidentiality which the user and/or the enterprise are required to adhere to. For example, it may be necessary for the data center to be in the same country as the device or to be a particular data center selected by a client. The rules or regulations pertaining to the data center location may be different depending on the country, on the type of device and/or on the method of communication with the cloud.

A second problem arising from lack of user control over the location of the data center is that a data center remote from the device location may result in communication delays, while a data center close to the device may provide a better user experience.

There therefore exists a need for a method of allowing the user to specify a particular data center or a particular geographic location of the data center to which the industrial measurement device will connect for transmitting or receiving data.

SUMMARY OF THE INVENTION

Accordingly, it is a general objective of the present disclosure to provide a system and method of allowing the user to specify a particular selected data center or a particular geographic location of the selected data center to which an industrial measurement device will connect for transmitting or receiving data.

It is a further objective to provide a system and method enabling the user to configure communication features for communication between the device and the selected data center.

It is a further objective to ensure that the data center is selected in accordance with any government, corporate or other regulations which pertain to the type of industrial measurement device, its geographic location and the geographic location of the selected data center.

DETAILED DESCRIPTION OF PREFERRED EMBODIMENT

Figure 1A:
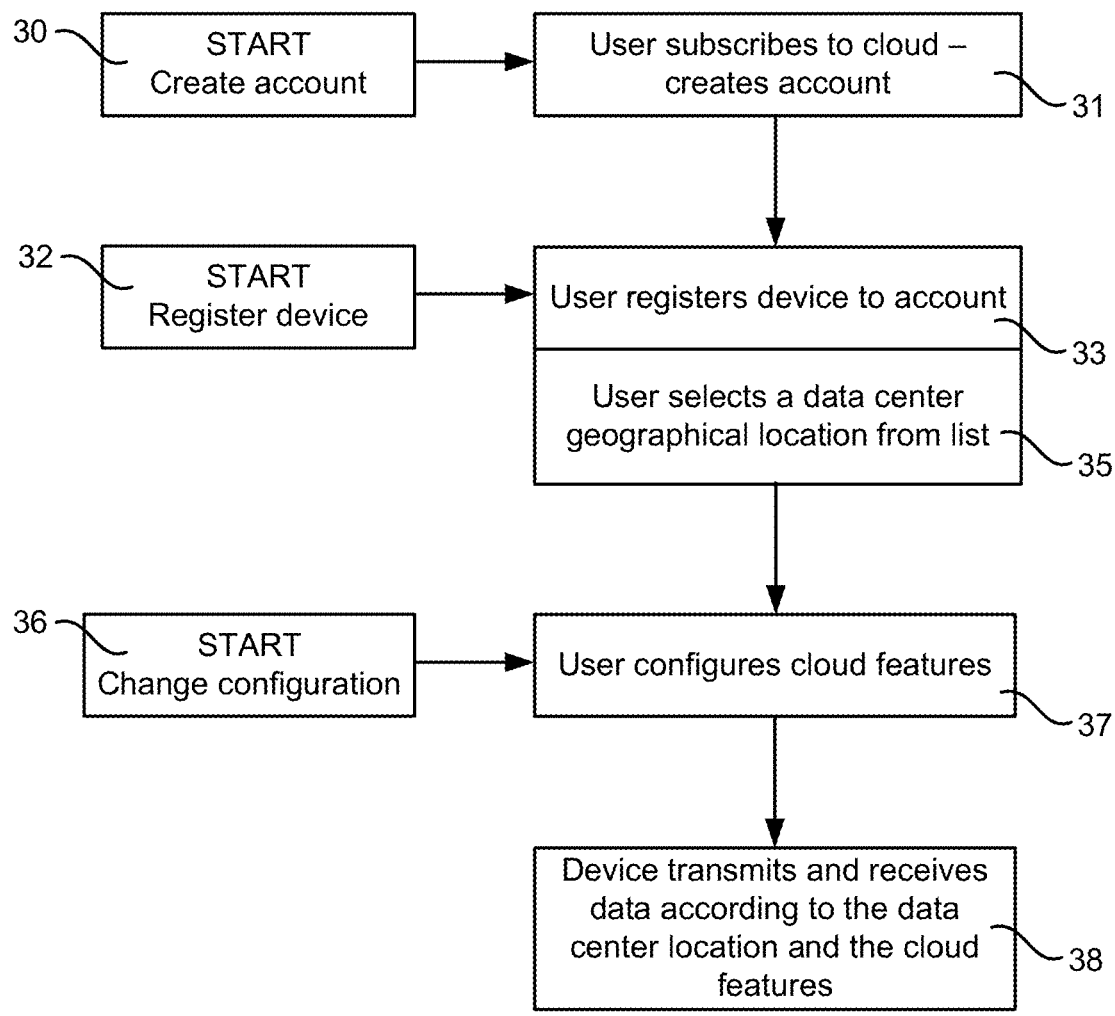
FIG. 1A is a schematic illustration of a method of data center localization according to the present disclosure.

FIG. 1A is a schematic illustration of a method of data center localization according to the present disclosure. Step 30 is the start of the method for the case of a user wishing to create a new account. In step 31, the user subscribes to the cloud and creates a personal account. In step 33 the user registers one or more devices to the account. As part of the registration process, in step 35 the user selects a geographical location of a data center from a list of available locations. Note that the user may also select the option of connecting to the data center which is closest to the geographical location of the device, where the geographical location of the device may be determined by GPS coordinates, the IP address, or any other suitable means. In step 37, the user has the opportunity to configure certain cloud features, which are described in connection with FIG. 3 below. In step 38 the device transmits and receives data in accordance with the selected data location and the selected cloud features.

For the case of a user who has already created an account but wishes to register a device, the start of the method is at step 32. For the case of a user who has already registered the device but wishes to change the device configuration, the start of the method is at step 36.

Figure 1B:
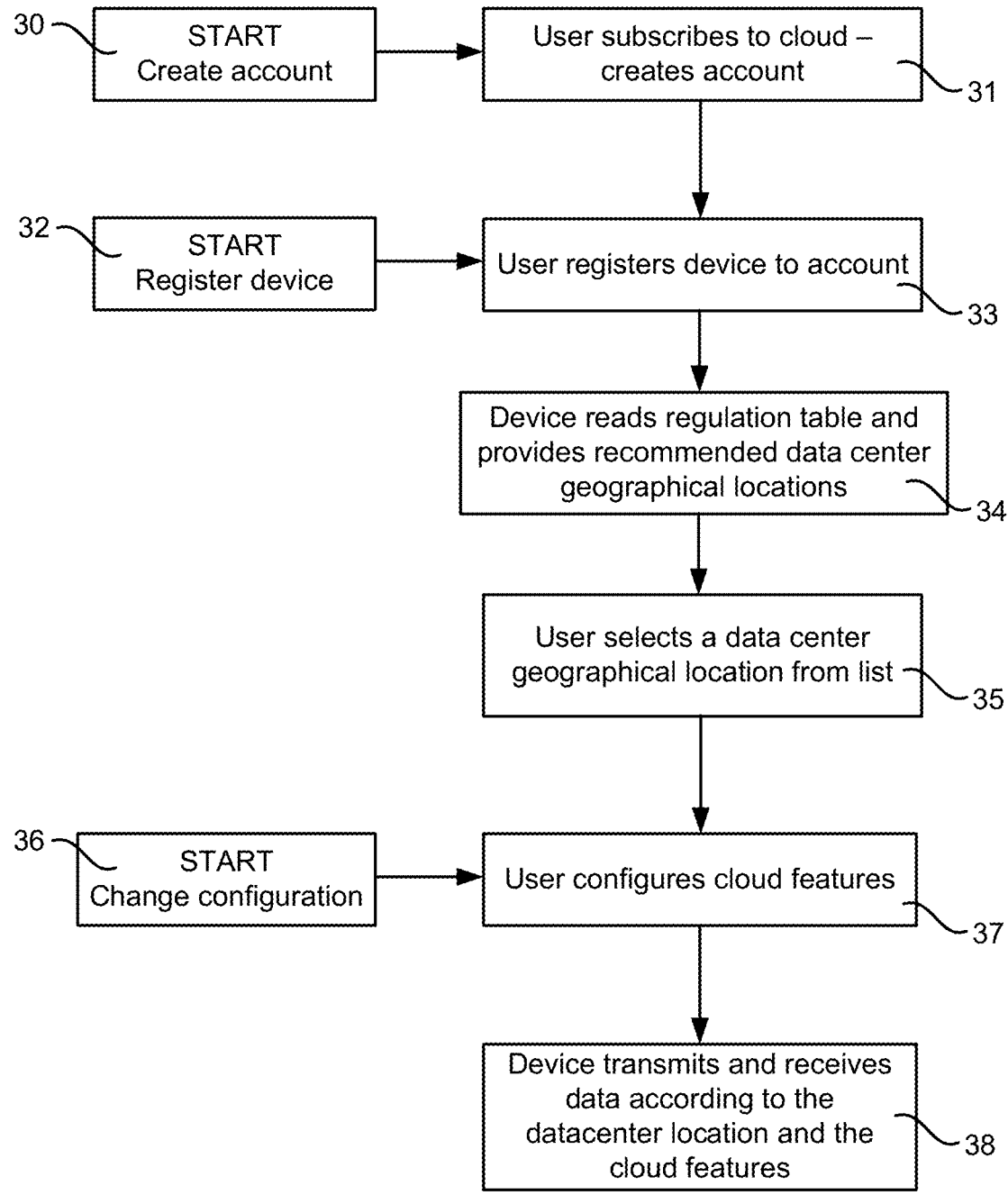
FIG. 1B is a schematic illustration of an alternative embodiment of a method of data center localization according to the present disclosure.

FIG. 1B is a schematic illustration of an alternative embodiment of a method of data center localization according to the present disclosure. The method of FIG. 1B includes an additional step 34 in which, after registration, the device reads a regulation table and provides a list of recommended data center locations. The regulation table contains information about government regulations specific to the location of the device and the type of device. The regulation table may be updated whenever regulations change. Note also that the regulation table may be stored either on the device or in the cloud, and the device may be configured to read the regulation table from the appropriate storage location.

Figure 2:
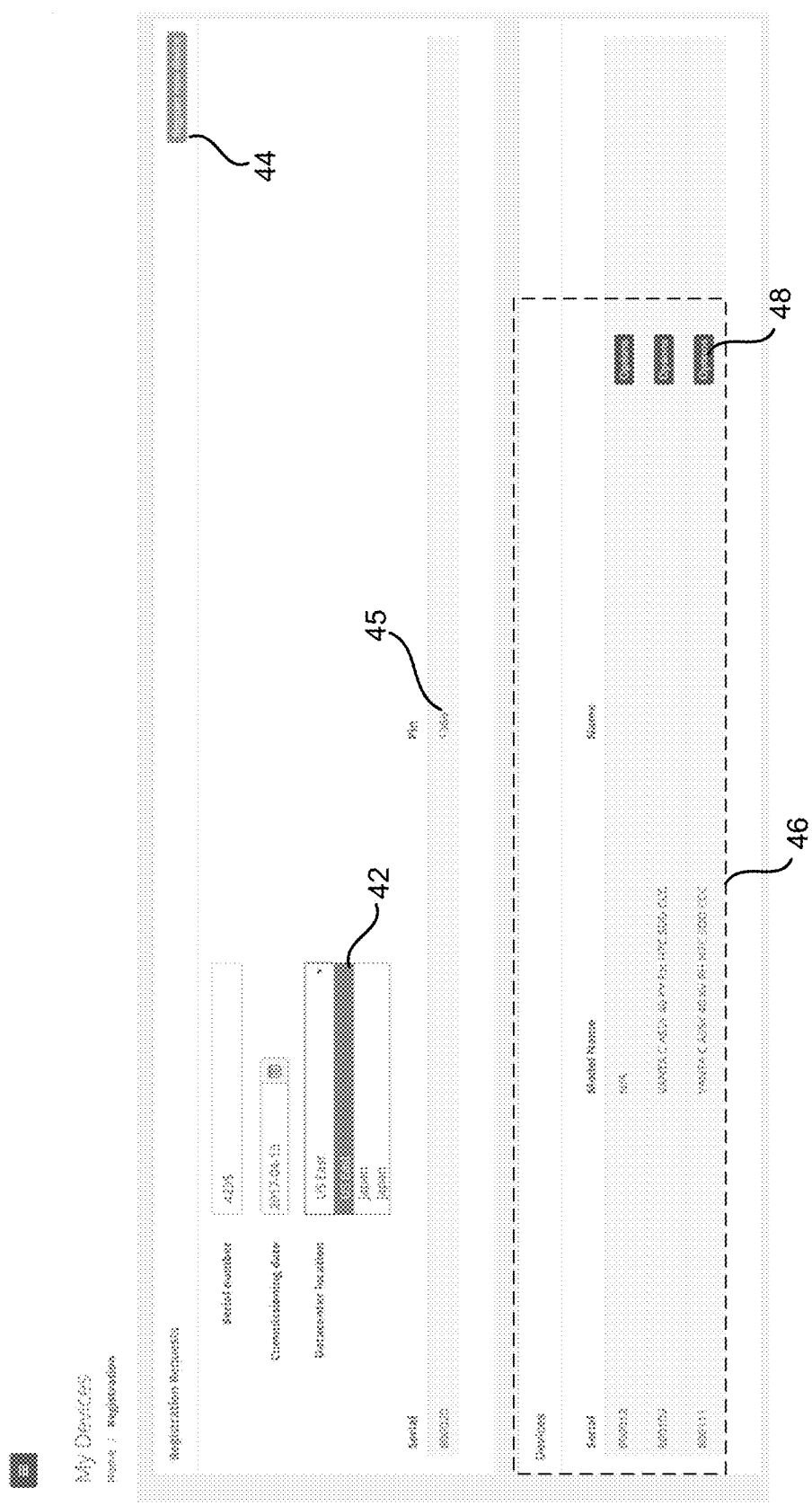
FIG. 2 is an exemplary user interface for selecting a data center geographical location and registering a device according to the present disclosure.

FIG. 2 shows an exemplary user interface for performing steps 33 and 35 of the method of FIG. 1A, namely selecting a data center geographical location and registering the device. A location selection box 42 allows the user to select the data center location—locations in US East and Japan are shown, but any relevant geographical location may be included in selection box 42. A button 44 is used to register the device, at which time a registration pin number 45 is generated allowing a two-factor authentication for subsequent user login, the two factors being the user account number and registration pin number 45. An area 46 of the user interface shows devices previously registered by this user, and options buttons 48 allow the cloud options of any of these devices to be reconfigured (see description in connection with FIG. 3 below).

Figure 3:
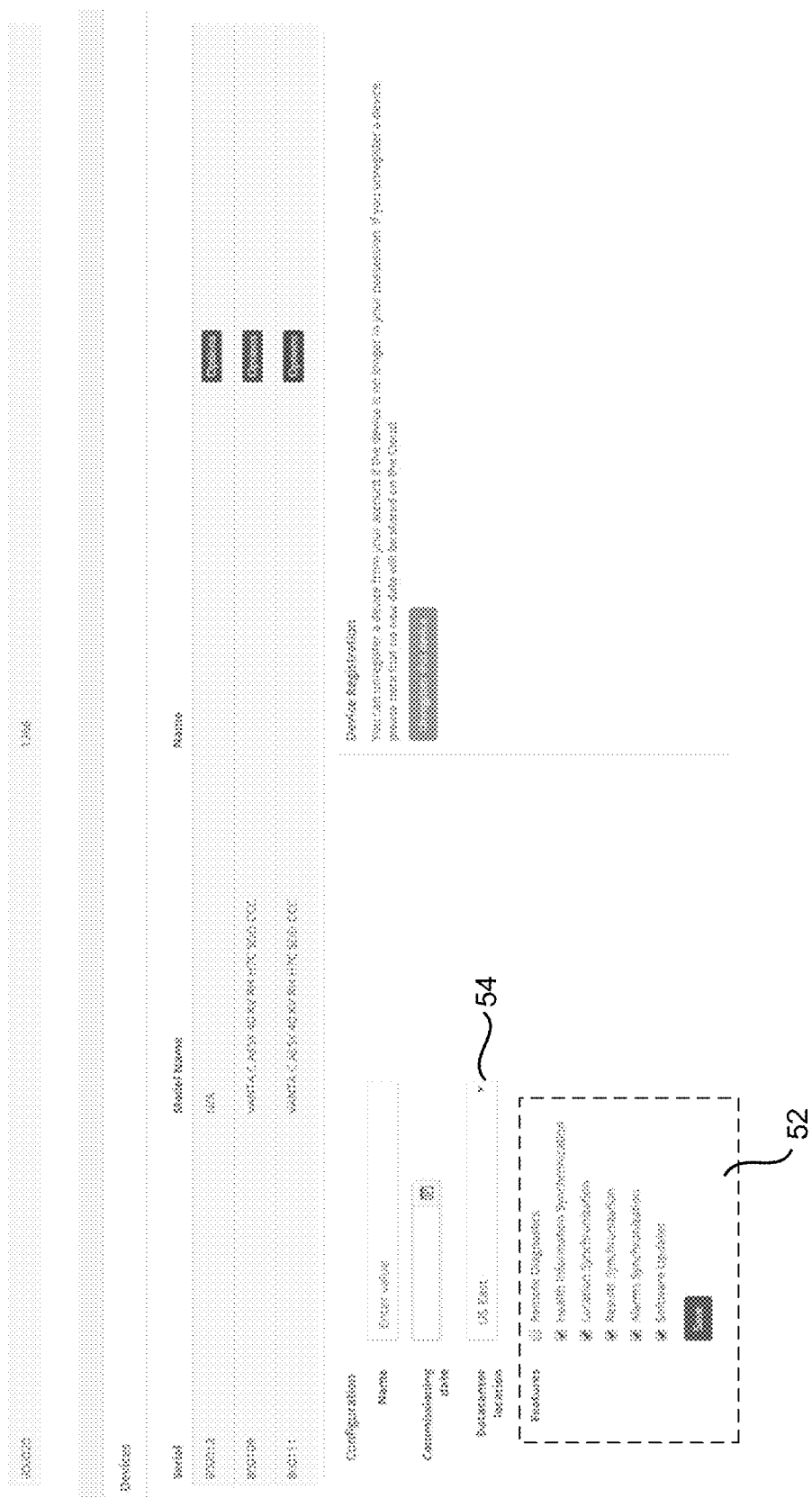
FIG. 3 is an exemplary user interface for configuring the cloud features of a registered device according to the present disclosure.

FIG. 3 shows an exemplary user interface for performing step 37 of the method of FIG. 1A, namely configuring or re-configuring the cloud features of a registered device. A cloud configuration box 52 may be used to enable or disable the following cloud features:

Remote diagnostics: when this feature is enabled, remote users may connect to the device for trouble-shooting and assistance.

Health information synchronization: when this feature is enabled, the device transmits information to the cloud about its health status or health parameters.

Location synchronization: when this feature is enabled, the device transmits information to the cloud about its geographical location. In a preferred embodiment, the device transmits its GPS location.

Results synchronization: when this feature is enabled, the device sends acquired inspection data to the cloud.

Alarms synchronization: when this feature is enabled, the device transmits information to the cloud about alarms.

Software updates: when this feature is enabled, the device may receive available software updates from the cloud. Note that information about the device model type and current software version is available in the cloud account of each registered device, and therefore the cloud features may be configured to send only updates compatible with the current software version. Alternatively the cloud features may be configured to send all updates, and the device may be configured to either accept only updates compatible with the current software version, or to accept updates only with explicit user permission. If device recalibration is required after a software update, a warning may be displayed, the cloud features may be configured to send such updates only if the device is located in a service center capable of performing the recalibration procedure, or the device may be configured to accept such updates only if the device is located in a service center capable of performing the recalibration procedure, or the device and/or the cloud features may be configured to send/accept such updates only with explicit user permission.

Note that the user interface of FIG. 3 also comprises a location re-selection box 54 which enables the user to reconfigure the data center location. The reconfigured data location may be different from the data center location selected at original registration of the device. Thus the data center location is also a configurable cloud feature.

Figure 4:
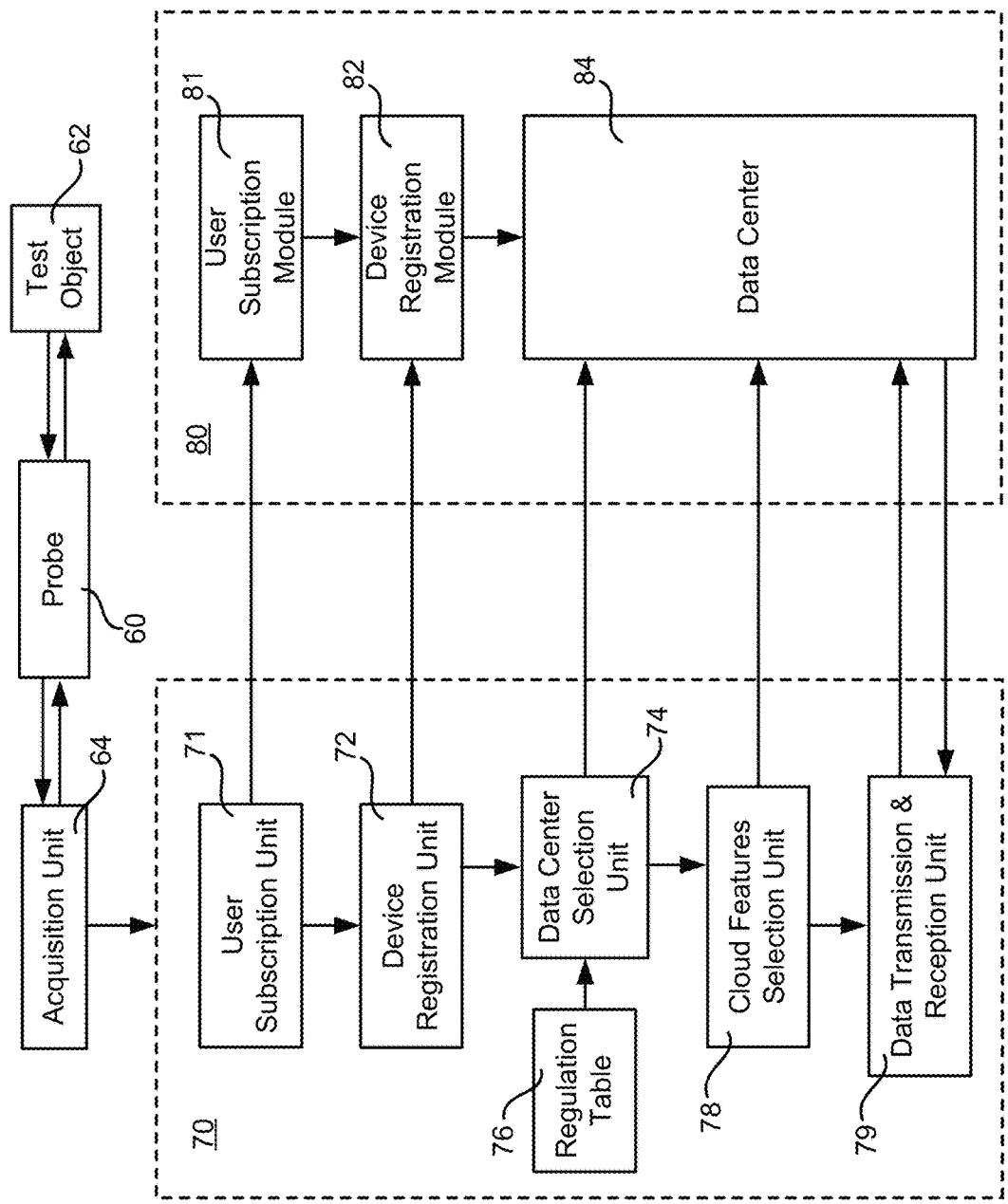
FIG. 4 is a schematic illustration of a system for data center localization according to the present disclosure.

FIG. 4 is a schematic illustration of a system for data center localization according to the present disclosure. An industrial measurement probe 60 is used to inspect a test object 62. Data from test object 62 received by probe 60 is acquired and digitized by an acquisition unit 64, and transmitted to an on-board computer system 70 located on the measurement device. On-board computer system 70 comprises a user subscription unit 71, a device registration unit 72, a data center selection unit 74, a cloud features selection unit 78 and a data transmission & reception unit 79. On-board computer system 70 communicates with a remote computer network 80. The communication method is preferably wireless, but any method of data transmission, including wired transmission, may be used and all such communication methods are within the scope of the present disclosure. Remote computer network 80 comprises a user subscription module 81, a device registration module 82 and a data center 84.

When a user wishes to create an account (step 31, FIG. 1A), user subscription unit 71 communicates with user subscription module 81. When the user wishes to register a device (step 33, FIG. 1A), device registration unit 72 communicates with device registration module 82. The user selects the location of data center 84 (step 35, FIG. 1A) by means of data center selection unit 74, and configures the cloud features (step 37, FIG. 1A) by means of cloud features selection unit 78. Data transmission & reception unit 79 is then responsible for interchange of data with data center 84 in accordance with the data center selection and the cloud features.

FIG. 4 includes an optional regulation table 76 which provides recommended data center locations to data center selection unit 74 (see step 34, FIG. 1B). As shown in FIG. 4, regulation table 76 resides within on-board computer system 70. However, regulation table 76 may also reside within remote computer network 80, in which case data center selection unit 74 communicates with remote computer network 80 in order to read recommended data locations from regulation table 76.

Although the present invention has been described in relation to particular embodiments thereof, it can be appreciated that various designs can be conceived based on the teachings of the present disclosure, and all are within the scope of the present disclosure.

What is claimed is:

1. A method associated with use of an industrial testing device, the method comprising:

retrieving, based on one or more government regulations associated with a type of the industrial testing device, a list of available data centers residing in a remote computer network external to the industrial testing device;

causing the list of available data centers to be displayed on a user interface;

receiving input from a user that selects a data center from the list of available data centers that are displayed in the user interface;

configuring communication features for communication between the industrial testing device and the selected data center, wherein the industrial testing device and the selected data center communicate in accordance with the communication features;

causing the user interface to display a plurality of industrial testing devices previously registered by the user; and receiving a user request to modify one or more features of a given industrial testing device of the plurality of industrial testing devices, wherein the one or more features includes a software updates feature that, when enabled, causes updates to be sent to the given industrial testing device when the given industrial testing device is located in a service center configured to perform recalibration of the given industrial testing device.

2. The method of claim 1, further comprising reading a regulation table, wherein the regulation table comprises recommended data center locations and wherein the selected data center is selected from the recommended data center locations.

3. The method of claim 2, wherein the industrial testing device is located in a device geographical location, and wherein the recommended data center locations are in accordance with regulations specific to the device geographical location.

4. The method of claim 2, wherein the regulation table is stored in a device memory located in the industrial testing device.

5. The method of claim 2, wherein the regulation table is stored in a remote memory located in the remote computer network.

6. The method of claim 1, wherein the selected data center is further selected based on a device geographical location of the industrial testing device.

7. The method of claim 1, further comprising updating a regulation table that includes the one or more government regulations associated with the type of the industrial testing device.

8. The method of claim 1, further comprising:
creating a user account in the remote computer network; and
registering the industrial testing device to the user account, wherein the list of available data centers is displayed after the industrial device is registered to the user account.

9. The method of claim 1, further comprising enabling the user to selectively enable and disable the one or more features in response to receiving the user request.

10. The method of claim 1, wherein the given industrial testing device is associated with a first data center location that is selected when the given industrial testing device was previously registered, further comprising enabling the user to reconfigure a data center location associated with the given industrial testing device in response to receiving the user request to associate the given industrial testing device with a second data center location different from the first data center location, wherein the industrial testing device and the remote computer network communicate wirelessly.

11. The method of claim 1, wherein the one or more features includes a remote diagnostics feature that, when enabled, allows the device to be remotely accessed for assistance or a health information synchronization feature that causes the device to transmit status information to a remove server.

12. A system configured for conducting industrial testing, the system comprising:
a plurality of data centers residing in a computer network coupled to an industrial testing device, the computer network being external to the industrial testing device, wherein the industrial testing device is configured to perform operations comprising:
retrieving, based on one or more government regulations associated with a type of the industrial testing device, a list plurality of data centers;
causing the list of data centers to be displayed on a user interface;
receiving input from a user that selects a data center from the list of data centers that are displayed in the user interface;
configuring communication features for communication between the industrial testing device and the selected data center;
transmitting a transmitted energy to a test object and receiving received signals from the test object;
receiving the received signals, and sending digitized received signals to the selected data center, wherein the industrial testing device communicates with the selected data center in accordance with the communication features;
causing the user interface to display a plurality of industrial testing devices previously registered by the user; and
receiving a user request to modify one or more features of a given industrial testing device of the plurality of industrial testing devices,
wherein the one or more features includes a software updates feature that, when enabled, causes updates to be sent to the given industrial testing device when the given industrial testing device is located in a service center configured to perform recalibration of the given industrial testing device.

13. The system of claim 12, wherein the selected data center is further selected based on a device geographical location of the industrial testing device.

14. The system of claim 12, further comprising operations for updating a regulation table that includes the one or more government regulations associated with the type of the industrial testing device.

15. The system of claim 12, further comprising operations for:
creating a user account in the computer network associated with a user; and
registering the industrial testing device to the user account, wherein the list of data centers is displayed after the industrial device is registered to the user account.

16. The system of claim 12, further comprising operations for enabling the user to selectively enable and disable the one or more features in response to receiving the user request.

17. A non-transitory computer readable medium comprising non-transitory computer readable instructions that, when executed by one or more processors, configure the one or more processors to perform operations comprising:
retrieving, based on one or more government regulations associated with a type of an industrial testing device, a list of available data centers residing in a remote computer network external to an industrial testing device, the list of data centers corresponding to a geographical location of the network;
causing the list of available data centers to be displayed on a user interface;
receiving input from a user that selects a data center from the list of available data centers that are displayed in the user interface;
configuring communication features for communication between the industrial testing device and the selected data center, wherein the industrial testing device and the selected data center communicate in accordance with the communication features;
causing the user interface to display a plurality of industrial testing devices previously registered by the user; and
receiving a user request to modify one or more features of a given industrial testing device of the plurality of industrial testing devices,
wherein the one or more features includes a software updates feature that, when enabled, causes updates to be sent to the given industrial testing device when the given industrial testing device is located in a service center configured to perform recalibration of the given industrial testing device.

* * * * *

UNITED STATES PATENT AND TRADEMARK OFFICE
CERTIFICATE OF CORRECTION

PATENT NO. : 10,785,303 B2
APPLICATION NO. : 15/941656
DATED : September 22, 2020
INVENTOR(S) : Ehab Ghabour Page 1 of 1

It is certified that error appears in the above-identified patent and that said Letters Patent is hereby corrected as shown below:

In the Claims

In Column 5, Line 42, in Claim 11, delete "remove" and insert --remote-- therefor Signed and Sealed this
Sixteenth Day of February, 2021

Drew Hirshfeld
*Performing the Functions and Duties of the
Under Secretary of Commerce for Intellectual Property and
Director of the United States Patent and Trademark Office*